(12) United States Patent
Hearn

(10) Patent No.: US 6,600,063 B1
(45) Date of Patent: Jul. 29, 2003

(54) DERIVATIVES OF PHENYL 4-AMINOSALICYLATE AND METHOD OF MAKING THE SAME

(75) Inventor: Michael J. Hearn, Needham, MA (US)

(73) Assignee: Board of Trustees of Wellesley College, Wellesley, MA (US)

( * ) Notice: Subject to any disclaimer, the term of this patent is extended or adjusted under 35 U.S.C. 154(b) by 55 days.

(21) Appl. No.: 09/694,638

(22) Filed: Oct. 23, 2000

(51) Int. Cl.$^7$ ............................................. C07C 229/00
(52) U.S. Cl. ........................................... 560/46; 560/23
(58) Field of Search ..................................... 560/46, 23

(56) References Cited

U.S. PATENT DOCUMENTS 2,604,488 A    7/1952  Friere

OTHER PUBLICATIONS

Chem. Abstr. 53: 11311 & 1958.*
Antibiotic and chemotherapy: anti–infective agents and their use in therapy, O'Grady, Francis et al.; Antibiotic and Chemotherapy, Chapter 37, pp. 501–504 (1997).
Principles of Medicinal Chemistry, Foye, William O.; Lemke, Thomas L.; Williams, David A., Fourth Edition, pp. 116–119; pp. 748–749; p. 753; p. 758 (1995).
A new derivative of p–aminosalicylic acid. The p–aminophenylsalicylate of FR7. Tuberculostatis activity in vitro and in mic. Freire, Santiago; Rist, Noel; Grumbach, Francoise. Inst. Pasteur, Paris, Ann. inst. Pasteur (1951), 81 407–23. (abstract only).
A new derivative of P.A.S. phenyl para–amino–salicylate or FR7. tuberculostatis activity in vitro and in mice, Freire, Santiago Americano; Rist, Noel; and Grumbach, Francoise; Pasteur Institute Tuberculosis Research Laboratories, pp. 407–409 (translation included) (1951).
Abstract of Derivatives of p–aminosalicylic acid, Takeda Chemical Industries, Ltd. (by Jiro Koromogawa and Yoichi Sawa). Japan. 4217('62), Jun. 12, Appln. May 27, 1960 2pp., vol. 58, Noncondensed Aromatic Compounds, pp. 10130–10131.
Abstract of Derivatives of p–aminosalicylic acid, Walter Huckel and Kurt Janecka, (Univ. Tubingen, Ger.). Arch. Pharm. 284, 341–51 (1951), vol. 47, Organic Chemistry p. 4305.

Abstract of Aryl p–aminosalicylate, Sutekichi Maruyama and Hisashi Imamura, (to Takedo Pharmaceutical Industries Co.). Japan. 4167952), Oct. 14., vol. 48, Organic Chemistry, p. 5221, 1966.
Abstract of A new derivative of p–aminosalicylic acid. The p–amino phenylsalicylate of FR 7. Tuberculostatic activity in vitro and in mice. Santiago Freire, Noel Rist, and Francoise Grumbach (Inst. Pasteur, Paris). Ann. inst. Pasteur 81, 407–23 (1951)., vol. 46, Chemical Abstracts, p. 9711.
Abstract of Synthesis of p–aminosalicylic acid, its derivatives, and analogous compound with Raney nickel, I. Makoto Suzuki, (Osaka Munic. Hyg. Lab.). J. Pharm. Soc. Japan 74, 703–6 (1954), vol. 49, Chemical Abstracts, p. 11595–11596.
Abstract of Tuberculostatic properties of p–aminosalol (phenyl p–aminosalicylate), Rolf Brodersen, Kirsten Bunch–Christensen and Leif Tybring (Leo Pharmaceutical Co., Copenhagen). Acta Pharmacol. et Toxicol. 11, 307–18 (1955), vol. 50, Chemical Abstracts, p. 2847.
Antimycobacterial activities of isoxyl and New Derivatives through the inhibition of mycolic acid synthesis. Benjawan Phetsuksiri et al., vol. 43, No. 5, Antimicrobial Agents and Chemotherapy, May 1999, p. 1042–1051.
The role of the metabolism of p–aminosalicylic acid (PAS) in the treatment of tuberculosis, Jorgen Lehman, vol. 50, Scand. J. resp. Dis., 1969) pp. 169–185.
Serum Concentrations of the Antimycobacterial Drugs, pp. 1154–1155, May 1998, Chest, vol. 113, issue 5.

* cited by examiner

*Primary Examiner*—Paul J. Killos
(74) *Attorney, Agent, or Firm*—Samuels, Gauthier & Stevens, LLP

(57) ABSTRACT

The present invention relates to novel antimycobacterial compounds and in particular to antimycobacterial compounds comprised of derivatives of phenyl 4-aminosalicylate. This invention further relates to methods for their preparation, to their use as therapeutic agents and to pharmaceutical compositions containing them. The novel methods of the invention yield derivatives of phenyl 4-aminosalicylate on a multi-gram scale and in high purity for subsequent biological evaluation in drug discovery.

24 Claims, No Drawings

DERIVATIVES OF PHENYL 4-AMINOSALICYLATE AND METHOD OF MAKING THE SAME

BACKGROUND OF THE INVENTION

1. Field of the Invention

The present invention relates to novel antimycobacterial compounds or pharmaceutically acceptable derivatives thereof, and methods for making the same. More specifically, this invention relates to novel derivatives of phenyl 4-aminosalicylate or pharmaceutically acceptable derivatives thereof, and methods for making the same. The compounds and pharmaceutical compositions of this invention may be advantageously used as agents against mycobacterial infections.

2. Description of the Related Art

The designation of tuberculosis as a global public health crisis by the World Health Organization in the mid-1990's has underscored the stern challenges facing the research community. The occurrence of some three million new cases of tuberculosis per year world-wide and the emergence of new strains of *Mycobacterium tuberculosis* characterized by drug resistance or increased virulence have made clear the pressing need for the evolution of newer and more powerful drugs. Moreover, several other mycobacterial diseases have begun to emerge, caused by nontuberculous mycobacteria. These include diseases caused by *Mycobacterium avium, Mycobacterium ulcerans, Mycobacterium marinum, Mycobacterium kansasii* and *Mycobacterium haemophilum*.

It is has been known in the art that phenyl 4-aminosalicylate has value as an antituberculosis compound. Tests have suggested that phenyl 4-aminosalicylate destroys the virulent strain of *M.tuberculosis* (H37Rv) even better than 4-aminosalicylic acid, a standard widely-used antituberculosis drug to which it is structurally related. (U.S. Pat. No. 2,604,488 (to Soc. Usines Chim. Rhone-Poulenc); Chemical Abstracts, vol. 48, 12807 c (1954).) The present invention provides useful, novel antimycobacterial compounds, namely derivatives of phenyl 4-aminosalicylate, which are effective against a number of species of mycobacteria.

In addition to the need for the evolution of newer and more powerful antimycobacterial drugs, the biological evaluation of compounds suspected to be active against mycobacteria requires that the compounds be readily available in pure form on quantity scale, generally understood to be gram or multi-gram scale, as opposed to milligram scale. Gram scale quantities are necessary for the large numbers of biological tests which must be performed and replicated for the evaluation of a new drug candidate.

Products of synthetic reactions are most desirable when they can be easily and cheaply obtained as dry and free-flowing solids. In the long run, dry and free-flowing solids permit better formulations of drugs as tablets, capsules or syrups. The invention disclosed herein provides a novel method of phenyl 4-aminosalicylate derivative synthesis which yields products directly as dry free-flowing solids in analytically pure form. The products of the prior art syntheses are obtained as intractable oils which are difficult and labor-intensive to purify or bring into dry free-flowing form. The present invention overcomes these drawbacks and provides methods of phenyl 4-aminosalicylate derivative synthesis which yield products that are suitable for biological evaluation or for further chemical transformation to other derivatives of phenyl 4-aminosalicylate.

BRIEF SUMMARY OF THE INVENTION

Broadly, the invention comprises novel derivatives of phenyl 4-aminosalicylate or pharmaceutically acceptable derivatives thereof, and methods for making the same. This invention further comprises methods for their preparation, to their use as therapeutic agents and to pharmaceutical compositions containing them. More particularly, this invention comprises methods of yielding novel derivatives of phenyl 4-aminosalicylate which have improved antimycobacterial activity and are comprised of structural elements which change the reaction chemistry and physical properties at the conjugation sites of phenyl 4-aminosalicylate during xenobiotic transformation. This invention further provides a method of yielding novel derivatives of phenyl 4-aminosalicylate having enhanced lipophilicity with respect to 4-aminosalicylic acid itself, signifying better permeation of the mycobacterial cell wall lipid domain and better drug action, on a multi-gram scale and in high purity for subsequent biological evaluation in drug discovery.

In one aspect, the invention comprises an antimycobacterial compound which comprises the formula:

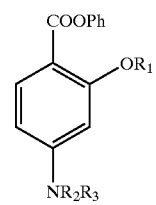

where $R_1$=H; and where $R_2$–$R_3$=$CHR_4$ where $R_4$=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle; or a pharmaceutically acceptable salt thereof; or a pharmaceutical isomer thereof; or a combination of the same.

Another aspect of the invention comprises an antimycobacterial compound which comprises the formula:

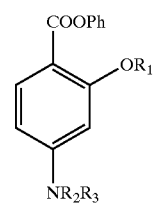

where $R_1$=H, $COR_5$ where $R_5$=$C_1$ to $C_{14}$ alkyl, $C_1$ to $C_{14}$ substituted alkyl, trifluoromethyl, trichloromethyl, dichloromethyl, chloromethyl, trideuteriomethyl, iodomethyl, $C_1$ to $C_{10}$ alkoxy, $C_1$ to $C_{10}$ substituted alkoxy, benzyloxy, substituted benzyloxy, steroidal, propenyloxy, difluorochloromethyl, pentafluoroethyl, perfluoropropyl, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

where $R_2$=H; and where $R_3$=$COR_6$ where $R_6$=$C_1$ to $C_{14}$ alkyl, $C_1$ to $C_{14}$ substituted alkyl, trifluoromethyl, trichloromethyl, dichloromethyl, chloromethyl, trideuteriomethyl, iodomethyl, $C_1$ to $C_{10}$ alkoxy, $C_1$ to $C_{10}$ substituted alkoxy, benzyloxy, substituted benzyloxy, steroidal, propenyloxy, difluorochloromethyl, pentafluoroethyl, perfluoropropyl, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

or a pharmaceutically acceptable salt thereof; or a pharmaceutical isomer thereof; or a combination of the same.

Another aspect of the invention comprises an antimycobacterial compound of the formula:

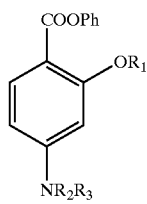

X where $R_1$=H, $COCH_3$, $COCH_2CH_3$;
where $R_2$=H; and
where $R_3$=$COCH_3$, $COCH_2CH_3$, $CSNHC_6H_5$, CSNH-4-$C_6H_4Br$, CSNH-4-$C_6H_4CH_3$, CSNH-4-$C_6H_4Cl$, $CSNHCH_2CH_3$, $CSNHCH(CH_3)_2$, $CSNHC(CH_3)_3$, CSNH-3-pyridyl, CSNH-2,3,4-$C_6H_2F_3$, CSNH-4-$C_6H_4F$, CSNH-3,5-$C_6H_3F_2$, CSNH-2,6-$C_6H_3F_2$, CSNH-2-Cl-4-$NO_2C_6H_3$, CSNH-2-F-4-$BrC_6H_3$, CSNH-4-$C_6H_4NO_2$, CSNH-3-$CF_3$-4-Cl—$C_6H_3$, CSNH-2-F-5-$CF_3$-$C_6H_3$, CSNH-2-$CF_3$-4-F—$C_6H_3$, CSNH-3-$CF_3$-4-F—$C_6H_3$, CSNH-2-$C_6H_4OCF_3$, CSNH-4-$C_6H_4OCF_3$, CSNH-4-$C_6H_4CF_3$, CSNH-2-$C_6H_4SCF_3$, CSNH-3-$C_6H_4CN$, CSNH-4-$C_6H_4CN$, CSNH-2-$C_6H_4OCHF_2$, CSNH-4-$C_6H_4OCHF_2$, CSNH-4-$C_6H_4OCH_3$, CSNH-3-$C_6H_4CH_3$, CSNH-2-$OCH_3$-4-$NO_2C_6H_4$, CSNH-4-$C_6H_4SCH_3$, CSNH-3,5-$(CF_3)_2$-$C_6H_4$, CSNH-3,4,5-$(CH_3)_3C_6H_2$, CSNH-1-naphthyl and CSNH-2-naphthyl; or a pharmaceutically acceptable salt thereof; or a pharmaceutical isomer thereof; or a combination of the same.

Another embodiment of the invention comprises an antimycobacterial compound of the formula:

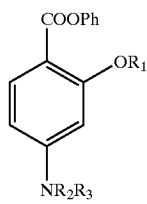

X where $R_1$=H, $COCH_3$, $COCH_2CH_3$; and where $R_2$=H; and where $R_3$=$COCH_3$, $COCH_2CH_3$, $CSNHC_6H_5$, CSNH-4-$C_6H_4Br$, CSNH-4-$C_6H_4CH_3$, CSNH-4-$C_6H_4Cl$; or a pharmaceutically acceptable salt thereof; or a pharmaceutical isomer thereof; or a combination of the same.

Another aspect of the invention comprises the formula X wherein $R_1$=H, $R_2$=H, and $R_3$=$CSNHC_6H_5$, CSNH-4-$C_6H_4Br$, CSNH-4-$C_6H_4CH_3$ and CSNH-4-$C_6H_4Cl$.

In yet another aspect, the invention comprises the formula X wherein $R_1$=H, and $R_2$-$R_3$=CH-2-$C_6H_4NO_2$, CH-4-$C_6H_4NO_2$ and CH-4-$C_6H_4CHO$.

Yet another aspect of the invention comprises a compound of the formula:

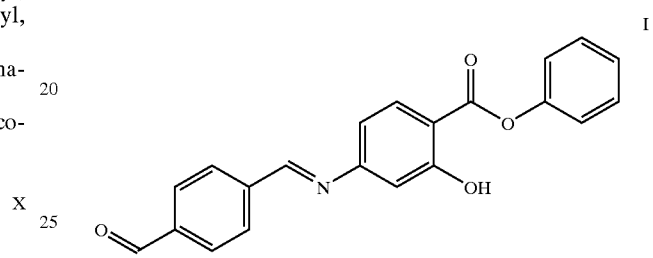

I wherein the compound exhibits enhanced and unexpected activity against mycobacteria selected from the group consisting of *M.tuberculosis*.

Another aspect of the invention comprises a compound of the formula:

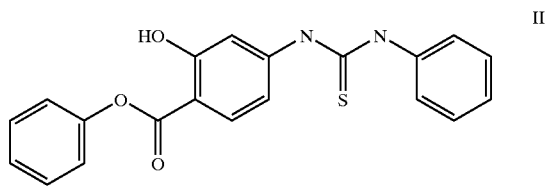

II wherein the compound exhibits enhanced and unexpected activity against mycobacteria selected from the group consisting of *M.tuberculosis*.

In yet another aspect, the invention comprises the formula:

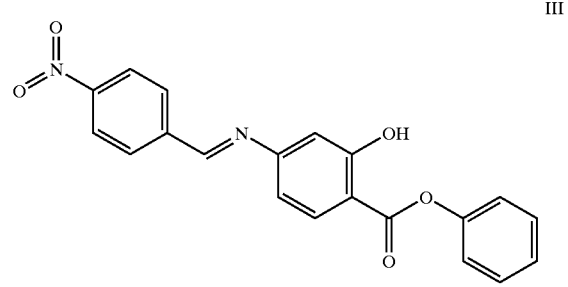

III wherein the compound exhibits enhanced and unexpected activity against mycobacteria selected from the group consisting of *M.tuberculosis*.

Another aspect of the invention comprises a compound of the formula:

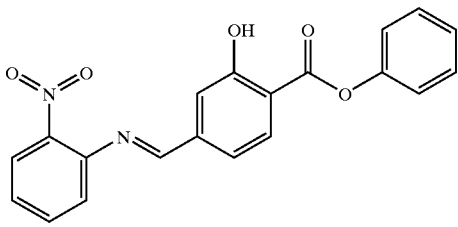

IV wherein the compound exhibits enhanced and unexpected activity against mycobacteria selected from the group consisting of *M.tuberculosis*.

In yet another aspect, the invention comprises a compound of the formula:

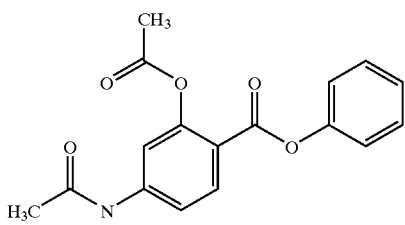

V wherein the compound exhibits enhanced and unexpected activity against mycobacteria selected from the group consisting of *M.tuberculosis*.

Suitable pharmaceutically-acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt, for example sodium, an alkaline earth metal salt, for example calcium or magnesium, an organic amine salt, for example triethylamine, morpholine, N-methylpiperidine, N-ethylpiperidine, procaine, dibenzylamine, N,N-dibenzylethylamine or amino acids, for example lysine. There may be more than one cation or anion depending on the number of charged functions and the valency of the cations or anions. A preferred pharmaceutically-acceptable salt is the sodium salt.

It is to be understood that certain compounds of formula X can exist in solvated as well as unsolvated forms such as, for example, hydrated forms. It is also to be understood that the invention encompasses all such solvated forms which possess antimycobacterial activity.

It is also to be understood that the invention relates to all tautomeric forms of compound of formula X that possess antimycobacterial activity. More particularly, it is to be understood that the invention encompasses all optical, diastereo- and regio-isomers of formula X that possess antimycobacterial activity.

The invention also broadly comprises the syntheses of the novel derivatives of phenyl 4-aminosalicylate. Further, the invention comprises the syntheses of novel derivatives of phenyl 4-aminosalicylate on multi-gram scale and in high purity for subsequent biological evaluation in drug discovery.

Another aspect of the invention comprises a method for synthesizing an antimycobacterial compound of the formula:

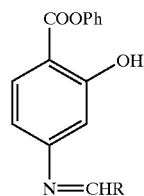

XI where R=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, which comprises adding para-aminosalicylic acid phenyl ester with a reactive aldehyde comprised of the formula:

RCHO where R=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, to form a reaction mixture. The reaction mixture is characterized in that the mole ratio of para-aminosalicylic acid phenyl ester to reactive aldehyde is about 0.93 to 1.00. The reaction mixture is refluxed and evaporated to form XI. The molar ratio is critical to the production of compound XI in a dry, free flowing solid form.

In yet another aspect, the invention comprises a method for synthesizing an antimycobacterial compound of the formula:

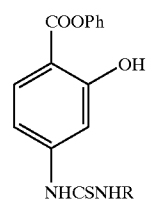

XII where R=$C_1$ to $C_{14}$ alkyl, $C_1$ to $C_{14}$ substituted alkyl, $C_2$ to $C_{10}$ alkenyl, $C_2$ to $C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, which comprises adding para-aminosalicylic acid phenyl ester with a mustard oil comprised of the formula:

RNCS where R=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, to form a reaction mixture. The reaction mixture is characterized in that the mole ratio of para-aminosalicylic acid phenyl ester to mustard oil is about 0.95 to 1.00. The reaction mixture is refluxed and cooled to produce XII. The molar ratio is critical to the production of compound XII in a dry, free flowing solid form.

Another aspect of the invention comprises a method for synthesizing an antimycobacterial compound of the formula:

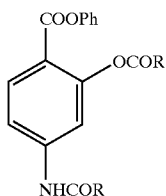

XIII where $R=C_1$ to $C_{14}$ alkyl, $C_1$ to $C_{14}$ substituted alkyl, trifluoromethyl, trichloromethyl, dichloromethyl, chloromethyl, trideuteriomethyl, iodomethyl, $C_1$ to $C_{10}$ alkoxy, $C_1$ to $C_{10}$ substituted alkoxy, benzyloxy, substituted benzyloxy, steroidal, propenyloxy, difluorochloromethyl, pentafluoroethyl, perfluoropropyl, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, which comprises adding para-aminosalicylic acid phenyl ester with a carboxylic acid anhydride comprised of the formula:

(RCO)$_2$O where $R=C_1$ to $C_{14}$ alkyl, $C_1$ to $C_{14}$ substituted alkyl, trifluoromethyl, trichloromethyl, dichloromethyl, chloromethyl, trideuteriomethyl, iodomethyl, $C_1$ to $C_{10}$ alkoxy, $C_1$ to $C_{10}$ substituted alkoxy, benzyloxy, substituted benzyloxy, steroidal, propenyloxy, difluorochloromethyl, pentafluoroethyl, perfluoropropyl, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, or with its synthetic equivalent, such as a mixed anhydride of the formula:

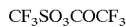

CF$_3$SO$_3$COCF$_3$ to form a reaction mixture. The reaction mixture is characterized in that the mole ratio of para-aminosalicylic acid phenyl ester to carboxylic acid anhydride is about 0.06 to 1.00. The reaction mixture is refluxed, cooled and dried to produce compound XIII. The molar ratio is critical to the production of compound XIII in a dry, free flowing solid form.

Another aspect of the invention comprises a method for synthesizing a compound comprised of the formula:

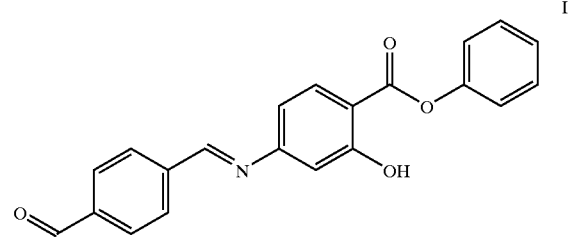

I which comprises adding para-aminosalicylic acid phenyl ester with para-terephthalaldehyde in absolute ethanol to form a reaction mixture, boiling the reaction mixture, refluxing the reaction mixture, distilling the reaction mixture and filtering the reaction mixture to yield compound I.

In yet another aspect, the invention comprises a method for synthesizing a compound comprised of the structure:

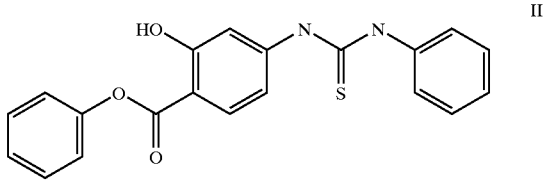

II which comprises adding para-aminosalicylic acid ester to absolute ethanol to form a reaction mixture, refluxing the reaction mixture, adding phenyl isothiocyanate to the reaction mixture to form a second reaction mixture, refluxing the second reaction mixture and cooling the second reaction mixture to yield II.

Another aspect of the invention comprises a method for synthesizing a compound comprised of the structure:

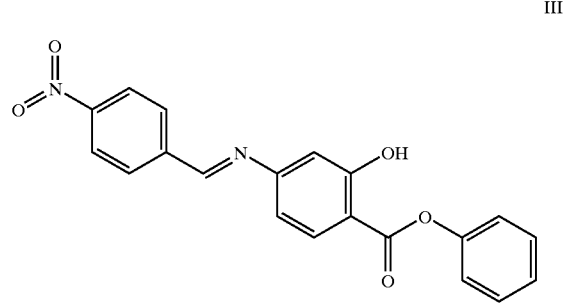

III which comprises adding para-aminosalicylic acid phenyl ester to para-nitrobenzaldehyde and ethanol to form a reaction mixture, refluxing the reaction mixture, distilling the reaction mixture, evaporating the reaction mixture to form a precipitate and washing and drying the precipitate to yield compound III.

In yet another aspect, the invention comprises a method for the synthesis of a compound comprised of the structure:

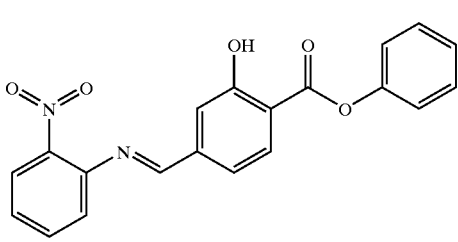

IV which comprises adding para-aminosalicylic acid phenyl ester to ortho-nitrobenzaldehyde and ethanol to form a reaction mixture, refluxing the reaction mixture, distilling the reaction mixture, evaporating the reaction mixture to form a precipitate and washing the precipitate and filtering the precipitate to yield compound IV.

Another aspect of the invention comprises a method for the synthesis of a compound comprised of the structure:

V which comprises adding para-aminosalicylic acid phenyl ester to acetic anhydride to form a reaction mixture, boiling and refluxing the reaction mixture, cooling the reaction mixture and drying the reaction mixture to yield compound V.

The pharmaceutical compositions of this invention may be prepared by combining the compound X of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition can be provided by employing conventional techniques. Preferably the composition is in unit dosage form containing an effective amount of the active component, that is, the compound of formula X according to this invention.

DESCRIPTION OF THE PREFERRED EMBODIMENT(S)

The invention will be described with reference to following non-limiting examples.

General Structural Outline for Synthesis of para-Aminosalicylic Acid Phenyl Ester Schiff Base

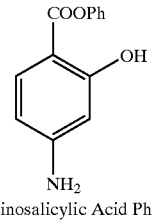

para-Aminosalicylic Acid Phenyl Ester + RCHO ---->

Reactive Aldehyde

Schiff Base

The para-aminosalicylic acid phenyl ester Schiff bases were prepared by the reactions of para-aminosalicylic acid phenyl ester with reactive aldehydes. The reaction conditions, which included reactions times, work-up methods, and methods for inducing crystallization, were critical and insured that the products of the syntheses were obtained in acceptable yield and purity.

para-Aminosalicylic acid phenyl ester and the appropriate reactive aldehyde were weighed into a round bottom flask. The volume of the flask was chosen in such a way that the contents of the entire reaction mixture did not exceed 50% of the flask's nominal capacity. The flask was fitted for reflux with a magnetic stirrer, temperature controlled heating mantle and reflux condenser. Sufficient absolute ethanol was added to make the resulting reaction mixture solution 0.13 Molar in para-aminosalicylic acid phenyl ester and 0.14 Molar in the reactive aldehyde. This characteristically made the mole ratio of para-aminosalicylic acid phenyl ester to reactive aldehyde to be about 0.93 to 1.00. The mixture was brought to the boiling point, and refluxing was continued for three hours. This amount of reflux time was necessary for complete conversion. During the three hours of refluxing, the reaction mixture can change color and can vary in color from light yellow to dark yellow, depending on the specific reactive aldehyde.

After three hours, half of the ethanol is distilled away, using a Dean-Stark trap as distillation apparatus. The solvent can be recovered and recycled for use in future procedures. The concentrated reaction mixture is turned out into a crystallizing dish and allowed to evaporate to form a solid. The solid is washed with several portions of ether, such that the total volume of ether is half of the volume of absolute ethanol used for the original reaction mixture. The infrared spectrum of this material showed the expected bands for the formation of the Schiff base, viz., infrared bands at ca. 3100, 1675 and 1300 $cm^{-1}$, diagnostic for the completion of the desired reaction.

The material was taken up in just the minimum volume of ethyl acetate required. After stirring for several minutes, petroleum ether (bp 30–60° C.) was added with care to the ethyl acetate solution in an amount of about ten times the volume of ethyl acetate that had been required thereby producing a cloudy mixture. The obtained mixture was allowed to stand over night, producing a well-defined solid material. The material was gravity filtered through Whatman No. 1 filter paper and dried on a porous porcelain plate to yield the Schiff base as a dry free-flowing solid. The tan to yellow solid obtained was analyzed by usual means, including the determination of physical constants, infrared and magnetic resonance spectroscopy and elemental analysis.

General Structural Outline for Synthesis of para-Aminosalicylic Acid Phenyl Ester Thioureide

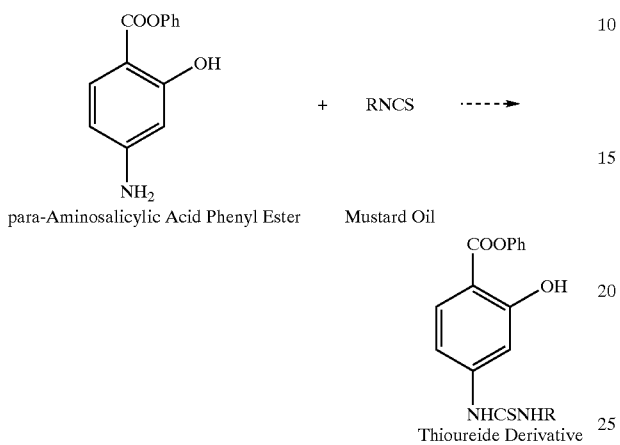

The para-aminosalicylic acid phenyl ester thioureides were prepared by the reactions of para-aminosalicylic acid phenyl ester with reactive mustard oils. The reaction conditions, which included reaction times, work-up methods, and methods for inducing crystallization, were critical and insured that the products of the syntheses were obtained in acceptable yield and purity.

para-Aminosalicylic acid phenyl ester was weighed into a round bottom flask. The volume of the flask was chosen in such a way that the contents of the entire reaction mixture did not exceed 50% of the flask's nominal capacity. The flask is fitted for reflux with a magnetic stirrer, temperature controlled heating mantle and reflux condenser. Sufficient absolute ethanol was added to make the resulting reaction mixture solution 0.3 Molar in para-aminosalicylic acid phenyl ester. The mixture was brought to reflux, producing a clear homogeneous solution. To this solution at the boil was added the appropriate mustard oil as a 0.17 Molar solution in absolute ethanol, at such a rate that vigorous reflux was maintained. The mustard oil was then washed in with a further portion of ethanol, equivalent in volume to the amount used to prepare the mustard oil solution. This characteristically made the mole ratio of para-aminosalicylic acid phenyl ester to mustard oil to be about 0.95 to 1.00. Thus there must be only a slight excess of the reactive mustard oil. Too much of the mustard oil leads to impure product. The mixture was maintained at the boiling point, and refluxing was continued for one hour. This amount of reflux time was necessary to ensure complete conversion. During the hour of refluxing, the reaction mixture can change color and can vary in color from light yellow to dark yellow, depending on the reactive mustard oil used.

After an hour, half of the ethanol was removed. This can be accomplished by boiling the ethanol off, using a simple hot plate, or the ethanol can be distilled away, using a Dean-Stark trap as distillation apparatus. The solvent can be recovered and recycled for use in future procedures. The concentrated reaction mixture was allowed to stand to cool over several hours thereby depositing a white solid, which was removed from the mother liquor by careful decantation. In a crystallizing dish, the solid was washed with two portions of ether, such that the total volume of ether was 40% of the volume of absolute ethanol used for the original reaction mixture. The solid was allowed to dry and was present as a dry free-flowing solid. The white solid obtained was analyzed by the usual means, including the determination of physical constants, infrared and magnetic resonance spectroscopy and elemental analysis.

General Structural Outline for Synthesis of para-Aminosalicylic Acid Phenyl Ester Diacyl Derivative

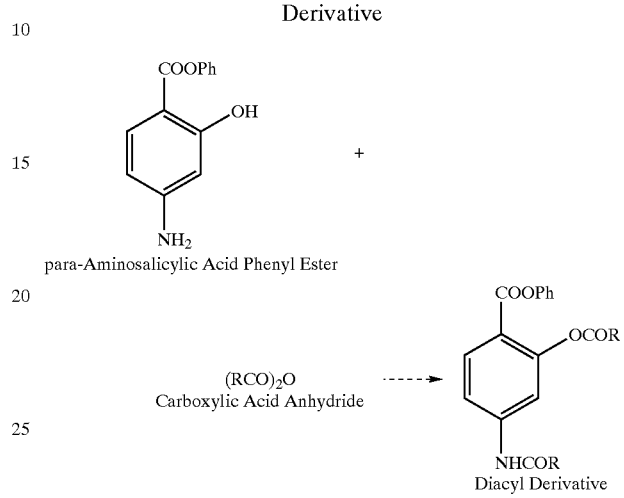

The para-aminosalicylic acid phenyl ester diacyl derivatives were prepared by the reactions of para-aminosalicylic acid phenyl ester with carboxylic acid anhydrides. Reaction conditions, which included reaction times, work-up methods, and methods for inducing crystallization, were critical and insured that the products of the syntheses are obtained in acceptable yield and purity.

para-Aminosalicylic acid phenyl ester was weighed into a round bottom flask. The volume of the flask was chosen in such a way that the contents of the entire reaction mixture did not exceed 50% of the flask's nominal capacity. The flask was fitted for reflux with a magnetic stirrer, temperature controlled heating mantle and reflux condenser.

Sufficient carboxylic acid anhydride, such as acetic anhydride, was added to make the resulting reaction mixture a 0.63 Molar solution of para-aminosalicylic acid phenyl ester in anhydride. This characteristically makes the mole ratio of para-aminosalicylic acid phenyl ester to anhydride to be about 0.06 to 1.00. The mixture was gradually brought to the boiling point over 10 minutes, and refluxed for twenty minutes.

The mixture was allowed to cool to room temperature and to stand for two hours, then poured out onto a watch glass and allowed to dry. The resulting solid residue was ground with an amount of ether equivalent in volume to the volume of anhydride used in the original reaction. The ether was drawn off, and the process was repeated. The solid was allowed to dry to yield the diacyl derivative as a dry free-flowing solid. The white solid obtained was analyzed by usual means, including the determination of physical constants, infrared and magnetic resonance spectroscopy and elemental analysis.

EXAMPLES

General Methods and Materials

Elemental analyses were performed by Galbraith Laboratories, Knoxville, Tenn. Melting points (mp) were taken in open capillary tubes using a Mel-Temp apparatus, measured in degrees Centigrade (° C.) and are corrected, unless otherwise specified in individual procedures. Infrared (IR) spectra were recorded on a Perkin-Elmer Model 1600 Fourier transform spectrophotometer as Nujol mulls and are reported in wavenumbers (v, cm$^{-1}$). Except as specified in the individual procedures, reactants and reagents were obtained from Aldrich Chemical Company and were used as received. Proton nuclear magnetic resonance (NMR) spectra were taken on Bruker 200 or 300 megahertz (MHz) Fourier transform instruments in dimethyl sulfoxide-d6 and are reported in parts per million delta (δ) downfield from internal tetramethylsilane as reference, with the operating field strength at 300 MHz, except as noted in individual procedures. High resolution mass spectra (HRMS) and low resolution mass spectra were determined at the National Institutes of Health Mass Spectrometry Facility at Michigan State University, East Lansing, Mich.

Abbreviations: After the first mention of the appropriate measured quantity in the text, standard abbreviations were used for masses in grams (g); volumes in milliliters (mL); quantities in millimoles (mmol); magnetic resonance field strengths in megahertz (Mhz); relative signal strengths in proton NMR (H); proton NMR coupling constants (J) in cycles per second (cps); proton multiplicities as singlets (s), doublets (d), triplets (t) and multiplets (m).

Representative Procedure for the Formation of a Schiff Base of para-Aminosalicylic Acid Phenyl Ester. Compound I, Schiff Base Preparation of the mono-para-Terephthalal of para-Aminosalicylic Acid Phenyl Ester. This compound was prepared using the General Structural Outline for Synthesis of para-Aminosalicylic Acid Phenyl Ester Schiff Bases. To para-terephthalaldehyde (0.85 g, 6.3 mmol) in boiling absolute ethanol (25 mL) in a 100 mL round bottom flask fitted for reflux was added a hot solution of para-aminosalicylic acid phenyl ester (1.33 g, 5.8 mmol) in absolute ethanol (25 mL) in several portions (5×5 mL) over a period of several minutes, such that refluxing never stopped. There was an immediate color change to a brown solution after the first addition. Reflux was continued for 90 minutes, and during the latter part of this reflux period 20 mL of ethanol was distilled out of the reaction mixture. This produced a yellow solid within the mixture. The analytical sample was obtained by gravity filtration of the hot reaction mixture to obtain the yellow solid, the title compound (0.397 g, 20%), mp 184° C., IR v 3199, 1679, 1630, 1611, 1569, 1490, 1342, 1312, 1300, 1256, 1199, 1142, 1104, 1067, 971, 876, 842, 818, 771, 735 cm$^{-1}$; NMR δ 10.5 (1H, br s), 6.9–8.2 (m, 14H). A second batch was obtained by evaporation of the mother liquor (total yield, 1.46 g, 73%), in such purity as to be suitable for further transformations.

Analysis. Calculated for $C_{21}H_{15}NO_4$: C, 73.04; H, 4.38. Found: C, 72.91; H, 4.68.

Representative Procedure for Formation of a Thioureide of para-Aminosalicylic Acid Phenyl Ester. Compound II, Phenylthioureide Formation of 4-Thioureido-2-hydroxybenzoic Acid Phenyl Ester. This compound was prepared using the General Structural Outline for Synthesis of para-Aminosalicylic Acid Phenyl Ester Thioureides. para-Aminosalicylic acid phenyl ester (1.36 g, 5.94 mmol) was weighed into a 100 mL round bottom flask fitted for reflux. Absolute ethanol (20 mL) was added, and the mixture was brought to reflux. To this clear homogeneous solution at the boil was added phenyl isothiocyanate (0.84 g, 6.22 mmol) dissolved in ethanol (5 mL) at such a rate that reflux was maintained. The mustard oil was washed in with a further portion of ethanol (5 mL), and the solution had taken on a yellow color. Refluxing was continued for one hour. The heat was removed, and the solution was allowed to stand over night. The solution was transferred to a 250 mL Florence flask and concentrated to half volume on a hot plate, then allowed to stand to cool over several hours. A white solid was deposited. The solid was freed from the mother liquor by careful decantation, placed in a crystallizing dish and washed with 2×4 mL portions of diethyl ether. After drying one obtained the title compound (1.46 g, 68%), mp 140–142° C., IR v 3204, 1677, 1625, 1589, 1546, 1494, 1362, 1336, 1285, 1237, 1205, 1167, 1073, 1024, 1002, 990, 967, 906, 866, 820, 771, 749, 734, 694 cm$^{-1}$; NMR δ 10.2–10.4 (3H, 3 overlapping br singlets), 7.1–8.0 (m, 13H).

Analysis. Calculated for $C_{20}H_{16}N_2SO_3$: C, 65.92; H, 4.43. Found: C, 65.73; H, 4.44.

Representative Procedure for the Formation of a Schiff Base of para-Aminosalicylic Acid Phenyl Ester. Compound III, Schiff Base Preparation of the para-Nitrobenzal of para-Aminosalicylic Acid Phenyl Ester. This compound was prepared using the General Structural Outline for Synthesis of para-Aminosalicylic Acid Phenyl Ester Schiff Bases. para-Aminosalicylic acid phenyl ester (1.33 g, 5.8 mmoles) and para-nitrobenzaldehyde (0.93 g, 6.2 mmoles) were placed in a 100 ml round bottom flask fitted for reflux containing ethanol (25 mL). The mixture was brought to a boil. Solid was present from the start of the reflux. After several minutes, a further portion (20 mL) of ethanol was added. After 20 minutes, the solid had completely dissolved. After three hours of reflux, approximately half of the ethanol was distilled away, using a Dean-Stark trap as distillation apparatus. The concentration mixture was poured into a crystallizing dish and allowed to evaporate. The resulting yellow solid was washed with ether (3×10 mL) and further dried to give 1.08 g (51%) of yellow crystalline solid, the infrared spectrum of which was consistent with the formation of the Schiff base III. To obtain the analytical sample, the following method was used: taking note of the amount required, the compound was dissolved in the minimum volume of ethyl acetate. Then petroleum ether was carefully added in an amount approximately equal to ten times the volume of ethyl acetate—but not so much as to cause the compound to oil out. Over night, the cloudy mixture deposited well-defined solid material which could be readily isolated and dried on a clay plate to give a dry free-flowing solid, mp 168–170° C. (uncorr), IR v 3100, 1676, 1632, 1612, 1599, 1574, 1517, 1353, 1312, 1296, 1257, 1215, 1183, 1170, 1138, 1106, 1071, 969, 884, 855, 844, 787, 779, 757, 698 cm$^{-1}$; NMR δ 10.5 (1H, s), 8.85 (1H, s), 8.41 (2H, d, J=6 cps), 8.22 (2H, d, J=6 cps), 8.08 (1H, d, J=6 cps), 6.93–7.57 (m, 7H).

Analysis. Calculated for $C_{20}H_{14}N_2O_5$: C, 66.30; H, 3.89. Found C, 66.45; H, 4.09.

Representative Procedure for the Formation of a Schiff Base of para-Aminosalicylic Acid Phenyl Ester. Compound IV, Schiff Base Preparation of the ortho-Nitrobenzal of para-Aminosalicylic Acid Phenyl Ester. This compound was prepared using the General Structural Outline for Synthesis of para-Aminosalicylic Acid Phenyl Ester Schiff Bases. para-Aminosalicylic acid phenyl ester (1.33 g, 5.81 mmol) and ortho-nitrobenzaldehyde (1.00 g, 6.62 mmol) were placed in a 100 mL round bottom flask fitted for reflux containing ethanol (45 mL). The mixture was brought to the boil, and refluxing was continued for four hours. Approximately half of the ethanol was then distilled away. The concentrated mixture was poured onto a watchglass and allowed to evaporate. After standing for several days, a solid had begun to form. It was taken up in ether (50 mL). Petroleum ether (500 mL) was added to the ether with stirring. A small amount of insoluble material was filtered off by gravity. From the evaporating mother liquor was then obtained the title compound by gravity filtration and drying on the filter cake (0.42 g, 20%), mp 124° C. (uncorr), IR v 3150, 1679, 1632, 1610, 1589, 1569, 1521, 1297, 1256, 1207, 1186, 1158, 1134, 1074, 984, 966, 956, 876, 847, 822, 788, 774, 734, 697, 682 $cm^{-1}$; NMR δ 10.55 (1H, s), 8.9 (1H, s), 6.9–8.2 (m, 12H).

Analysis. Calculated for $C_{20}H_{14}N_2O_5$: C, 66.30; H, 3.89. Found: C, 66.08; H, 3.89.

Representative Procedure for the Formation of a Diacyl Derivative of para-Aminosalicylic Acid. Compound V, Diacyl Derivative Preparation of 2-Acetoxy-4-acetamidobenzoic Acid Phenyl Ester. This compound was prepared using the General Structural Outline for Synthesis of para-Aminosalicylic Acid Phenyl Ester Diacyl Derivatives. In a 50 mL pear shaped flask fitted for reflux were mixed para-aminosalicylic acid phenyl ester (1.45 g) and acetic anhydride (10 mL). Over 10 minutes, the mixture was brought to the boil, and refluxing was continued for 20 minutes. The mixture was allowed to cool to room temperature and stand for two hours, then poured out into a watchglass and allowed to dry. The resulting residue was ground with ether (10 mL) and the process repeated. The resulting white crystalline solid was the title compound (0.75 g, 38%), mp 142–143° C. (uncorr); IR v 3323, 1767, 1734, 1673, 1613, 1590, 1506, 1268, 1207, 1185, 1163, 1134, 1056, 1014, 1002, 944, 895, 862, 844, 748, 691 $cm^{-1}$; NMR δ 10.5 (1H, br s), 8.2–7.1 (m, 8H), 2.2 (3H, s), 2.1 (3H, s).

Analysis. Calculated for $C_{17}H_{15}NO_5$: C, 65.17; H, 4.83. Found: C, 65.08; H, 4.95.

Results
In vitro Testing Against *M. tuberculosis*

Primary screening was conducted at 12.5 or 6.25 ug/ml (or molar equivalent of highest molecular weight compound in a series of congeners) against *Mycobacterium tuberculosis* H37Rv (ATCC 27294) in BACTEC 12B medium using the Microplate Alamar Blue Assay (MABA). Compounds exhibiting fluorescence were tested in the BACTEC 460-radiometric system. Compounds effecting <90% inhibition in the primary screen (MIC>6.25 ug/ml) were not generally evaluated further. Compounds demonstrating at least 90% inhibition in the primary screen were re-tested at lower concentrations against *M. tuberculosis* H37Rv to determine the actual minimum inhibitory concentration (MIC) in the MABA. The MIC was defined as the lowest concentration effecting a reduction in fluorescence of 90% relative to controls. Concurrent with the determination of MICs, compounds were tested for cytotoxicity (IC50) in VERO cells at concentrations less than or equal to 62.5 ug/ml or 10 times the MIC for *M. tuberculosis* H37Rv. After 72 hours exposure, viability was assessed on the basis of cellular conversion of MTT into a formazan product using the Promega CellTiter 96 Non-radioactive Cell Proliferation Assay. Compounds for which the IC50:MIC (SI) ratio is >10 have in vitro activity confirmed in the BACTEC 460 at 6.25 ug/ml. Compounds were then tested for killing of *M. tuberculosis* Erdman (ATCC 35801) in monolayers of mouse bone marrow macrophages. (EC99 and EC90; lowest concentration effecting a 90% and 99% reduction in colony forming units at 7 days compared to drug-free controls) at 4-fold concentrations equivalent to 0.25, 1, 4 and 16 times the MIC. Concurrent with the testing of compounds in macrophages, MICs were determined in the MABA for three strains of drug-resistant *M. tuberculosis*, (each strain resistant to a single TB drug) as well as *M. avium*. Typically, all compounds progressing to this stage of screening were tested against *M. avium* (ATCC 25291), *M. tuberculosis* strains resistant to isoniazid (ATCC 35822), rifampin (ATCC 35838), and one other drug resistant strain (the latter determined by the compound type) as well as the drug-sensitive strains H37Rv and Erdman. Minimum bactericidal concentration (MBC) was then determined for *M. tuberculosis* H37Rv and Erdman (and the corresponding drug-resistant strain for analogs of known antitubercular drugs) by subculturing onto drug-free solid following exposure in supplemented Middlebrook 7H9 media to drug concentrations equivalent to and higher than the previously determined MICs of the respective strains.

Referring to following tables, the EC90 represents bacteriostatic activity, and the EC99 indicates bactericidal activity. The EC90 denotes the effective concentration to give a 90% reduction in intramacrophage bacteria relative to a drug-free control. Since this concentration maintains roughly the level of the initial inoculum, the value represents the necessary amount of drug to maintain a static level of bacteria within the macrophage host. The EC99 value represents a one log reduction and thus gives a measure of the bactericidal activity of the drug. The ratio EC90/MIC provides a measure of bioavailability and metabolism of the active agent within the living host, since it compares the in vitro activity against the bacillus to the activity against the bacillus while it lives within the host cell.

TABLE 1

| SAMPLE ID | STRUCTURE | TEST DATE | ASSAY | MIC (ug/ml) | % Inhibition | COMMENT |
|---|---|---|---|---|---|---|
| 133652 | 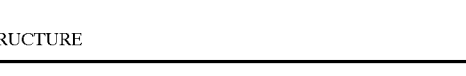 | Mar. 4, 1999 | BACTEC | <12.5 | 97 + | MIC of RMP +0.25 to 0.125 ug/ml vs. M. tuberculosis |

TABLE 2

| SAMPLE ID | STRUCTURE | % Inhibition | MIC (ug/ml) | ASSAY |
|---|---|---|---|---|
| 13352 | 4-nitrobenzylidene-amino-2-hydroxy-phenyl benzoate | 97 | 0.1 | BACTEC |

TABLE 3

| SAMPLE ID | STRUCTURE | TEST DATE | ASSAY | MIC (ug/ml) | % Inhibition | COMMENT |
|---|---|---|---|---|---|---|
| 130069 | 4-formylbenzylidene-amino-2-hydroxy-phenyl benzoate | Dec. 11, 1998 | Bactec | <12.5 | 99 | + MIC of RMP = 0.25 ug/ml vs. M. tuberculosis |

TABLE 4

| SAMPLE ID | STRUCTURE | MIC (ug/ml) | SI | EC90 | EC99 | EC90/MIC |
|---|---|---|---|---|---|---|
| 131326 | 2-hydroxy-4-(3-phenylthioureido)-phenyl benzoate | 0.2 | 35 | 0.203 | 0.92 | 1.02 |

TABLE 5

| SAMPLE ID | STRUCTURE | TEST DATE | ASSAY | MIC (ug/ml) | % Inhibition | COMMENT |
|---|---|---|---|---|---|---|
| 131326 | 2-hydroxy-4-(3-phenylthioureido)-phenyl benzoate | Dec. 15, 1998 | Bactec | <12.5 | 100 | + MIC of RMP = 0.25 ug/ml vs. M. tuberculosis |

TABLE 6

| SAMPLE ID | STRUCTURE | % Inhibition | ASSAY | MIC (ug/ml) |
|---|---|---|---|---|
| 131326 | (phenyl salicylate with 4-(3-phenylthioureido) substituent) | 100 | BACTEC | 0.2 |

TABLE 7

| SAMPLE ID | STRUCTURE | ASSAY | MIC (ug/ml) | % Inhibition |
|---|---|---|---|---|
| 138392 | (phenyl 2-(propanoyloxy)-4-(propanamido)benzoate) | ALAMAR | 0.39 | 94 |

TABLE 8

| SAMPLE ID | STRUCTURE | ASSAY | MIC (ug/ml) | % Inhibition |
|---|---|---|---|---|
| 139235 | (phenyl 2-hydroxy-4-((2-nitrophenylimino)methyl)benzoate) | ALAMAR | 0.025 | 97 |

TABLE 9

| SAMPLE ID | STRUCTURE | ASSAY | MIC (ug/ml) I | MIC H37Rv | MIC ERDMA (ug/ml) |
|---|---|---|---|---|---|
| 131326 | (phenyl salicylate with 4-(3-phenylthioureido) substituent) | BACTEC | 0.2 | 35 1.56 | 0.2 |

| SAMPLE ID | MIC INH-R (ug/ml) | INH-R: MIC | MIC RMP-R (ug/ml) | RMP-R: MIC | MIC EMB-R (ug/ml) | EMB-R MIC | MIC ETA-R (ug/ml) | ETA-R MIC |
|---|---|---|---|---|---|---|---|---|
| 131326 | <=0.1 | <=0.5 | 0.2 | 1 | 0.2 | 1 | 0.2 | 0.04 |

All journal articles and reference citations provided above, in parentheses or otherwise, whether previously stated or not, are incorporated herein by reference.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what I now claim is:

1. An antimycobacterial compound which comprises the formula:

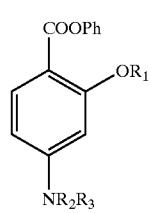

X where $R_1$=H; and where $R_2$–$R_3$=CHR$_4$ where $R_4$=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

or a pharmaceutically acceptable salt thereof; or a pharmaceutical isomer thereof; or a combination of the same.

2. The antimycobacterial compound according to claim 1 wherein $R_1$=H, and $R_2$–$R_3$=CH-2-$C_6H_4NO_2$, CH-4-$C_6H_4NO_2$ and CH-4-$C_6H_4$CHO.

3. An antimycobacterial compound which comprises the formula:

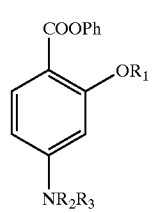

X where $R_1$=H, COR$_5$ where $R_5$=$C_1$ to $C_{14}$ alkyl, $C_1$ to $C_{14}$ substituted alkyl, $C_1$ to $C_{10}$ alkoxy, $C_1$ to $C_{10}$ substituted alkoxy, benzyloxy, substituted benzyloxy, steroidal, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

where $R_2$=H; and where $R_3$=COR$_6$ where $R_6$=$C_1$ to $C_{14}$ alkyl, $C_1$ to $C_{14}$ substituted alkyl, $C_1$ to $C_{10}$ alkoxy, $C_1$ to $C_{10}$ substituted alkoxy, benzyloxy, substituted benzyloxy, steroidal, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

or a pharmaceutically acceptable salt thereof; or a pharmaceutical isomer thereof; or a combination of the same.

4. A method for the synthesizing a compound comprised of the formula:

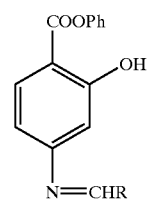

XI where R=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, which comprises:

adding para-aminosalicylic acid phenyl ester with a reactive aldehyde comprised of the formula:

RCHO where R=$C_1$ to $C_{14}$ alkyl, $C_1$ to $C_{14}$ substituted alkyl, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, to form a reaction mixture, the reaction mixture is characterized in that the mole ratio of para-aminosalicylic acid phenyl ester to reactive aldehyde is about 0.93 to 1.00;

refluxing the reaction mixture; and evaporating the reaction mixture to produce XI.

5. A method for synthesizing the compound comprised of the formula:

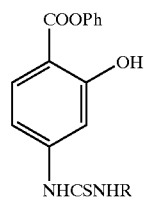

XII where R=$C_6H_5$, 4-$C_6H_4$Br, 4-$C_6H_4CH_3$, 4-$C_6H_4$Cl, $CH_2CH_3$, $CH(CH_3)_2$, $C(CH_3)_3$, 3-pyridyl, 2,3,4-$C_6H_2F_3$, 4-$C_6H_4$F, 3,5-$C_6H_3F_2$, 2,6-$C_6H_3F_2$, 2-Cl-4-$NO_2C_6H_3$, 2-F-4-Br$C_6H_3$, 4-$C_6H_4NO_2$, 3-$CF_3$-4-Cl—$C_6H_3$, 2-F-5-$CF_3$-$C_6H_3$, 2-$CF_3$-4-F—$C_6H_3$, 3-$CF_3$-4-F—$C_6H_3$, 2-$C_6H_4OCF_3$, 4-$C_6H_4OCF_3$, 4-$C_6H_4CF_3$, 2-$C_6H_4SCF_3$, 3-$C_6H_4CN$, 4-$C_6H_4CN$, 2-$C_6H_4OCHF_2$, 4-$C_6H_4OCHF_2$, 4-$C_6H_4OCH_3$, 3-$C_6H_4CH_3$, 2-$OCH_3$-4-$NO_2C_6H_4$, 4-$C_6H_4SCH_3$, 3,5-$(CF_3)_2$—$C_6H_4$, 3,4,5-$(CH_3)_3C_6H_2$, 1-naphthyl and 2-naphthyl, which comprises:
adding para-aminosalicylic acid phenyl ester with a mustard oil comprised of the formula:

RNCS where R=$C_6H_5$, 4-$C_6H_4Br$, 4-$C_6H_4CH_3$, 4-$C_6H_4Cl$, $CH_2CH_3$, $CH(CH_3)_2$, $C(CH_3)_3$, 3-pyridyl, 2,3,4-$C_6H_2F_3$, 4-$C_6H_4F$, 3,5-$C_6H_3F_2$, 2,6-$C_6H_3F_2$, 2-Cl-4-$NO_2C_6H_3$, 2-F-4-$BrC_6H_3$, 4-$C_6H_4NO_2$, 3-$CF_3$-4-Cl—$C_6H_3$, 2-F-5-$CF_3$-$C_6H_3$, 2-$CF_3$-4-F—$C_6H_3$, 3-$CF_3$-4-F—$C_6H_3$, 2-$C_6H_4OCF_3$, 4-$C_6H_4OCF_3$, 4-$C_6H_4CF_3$, 2-$C_6H_4SCF_3$, 3-$C_6H_4CN$, 4-$C_6H_4CN$, 2-$C_6H_4OCHF_2$, 4-$C_6H_4OCHF_2$, 4-$C_6H_4OCH_3$, 3-$C_6H_4CH_3$, 2-$OCH_3$-4-$NO_2C_6H_4$, 4-$C_6H_4SCH_3$, 3,5-$(CF_3)_2$—$C_6H_4$, 3,4,5-$(CH_3)_3C_6H_2$, 1-naphthyl and 2-naphthyl, to form a reaction mixture, the reaction mixture characterized in that the mole ratio of para-aminosalicylic acid phenyl ester to mustard oil is about 0.95 to 1.00;
refluxing the reaction mixture; and
cooling the reaction mixture to produce XII.

6. A method for synthesizing a compound comprising the formula:

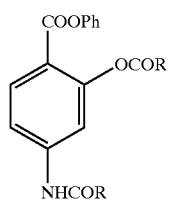

XIII where R=$C_1$ to $C_{14}$ alkyl, $C_1$ to $C_{14}$ substituted alkyl, $C_1$ to $C_{10}$ alkoxy, $C_1$ to $C_{10}$ substituted alkoxy, benzyloxy, substituted benzyloxy, steroidal, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle, which comprises adding para-aminosalicylic acid phenyl ester with a carboxylic acid anhydride comprised of the formula:

$(RCO)_2O$ where R=$C_1$ to $C_{14}$ alkyl, $C_1$ to $C_{14}$ substituted alkyl, $C_1$ to $C_{10}$ alkoxy, $C_1$ to $C_{10}$ substituted alkoxy, benzyloxy, substituted benzyloxy, steroidal, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

or with a mixed anhydride of the formula:

$CF_3SO_3COCF_3$ to form a reaction mixture, the reaction mixture characterized in that the mole ratio of para-aminosalicylic acid phenyl ester to carboxylic acid anhydride is about 0.06 to 1.00;

refluxing the reaction mixture;
cooling the reaction mixture; and
drying the reaction mixture to produce compound XIII.

7. The method of claim 4 which further comprises:
adding absolute ethanol to the reaction mixture.

8. The method of claim 7 wherein refluxing comprises:
refluxing for three hours.

9. The method of claim 8 which further comprises:
washing compound XI with ethyl acetate to form a solution.

10. The method of claim 9 which further comprises:
adding petroleum ether to the solution.

11. The method of claim 10 which further comprises:
filtering the solution to form a filtrate and drying the filtrate to produce a dry free flowing solid comprised of compound XI.

12. The method of claim 5 wherein refluxing comprises refluxing for one hour.

13. The method of claim 12 wherein the reaction mixture comprises a first reaction mixture and which further comprises:
adding absolute ethanol and the para-aminosalicylic acid phenyl ester to form a second reaction mixture of 0.3M in para-aminosalicylic acid phenyl ester;
refluxing the second reaction mixture to produce a clear homogenous solution;
adding the mustard oil as a 0.17M solution in absolute ethanol to the solution at a rate to maintain vigorous reflux;
washing the solution to produce the first reaction mixture.

14. The method of claim 13 which further comprises:
removing the absolute ethanol from the reaction mixture.

15. The method of claim 14 wherein cooling the reaction mixture comprises:
decanting compound XII from the reaction mixture;
washing compound XII with ether to form a second solution; and
drying the second solution to produce a dry free flowing solid comprised of compound XI.

16. The method of claim 6 wherein refluxing comprises:
refluxing for twenty minutes.

17. The method of claim 16 which further comprises:
adding ether to compound XIII to form a solution; and
drying the solution to produce a dry free flowing solid comprised of compound XIII.

18. An antimycobacterial compound which comprises the formula:

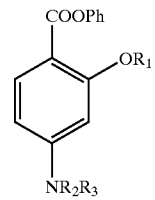

X wherein $R_1$=H, $COCH_3$, $COCH_2CH_3$, $R_2$=H, and $R_3$=$COCH_3$, $COCH_2CH_3$, $CSNHC_6H_5$, CSNH-4-$C_6H_4Br$, CSNH-4-$C_6H_4CH_3$, CSNH4-$C_6H_4Cl$, $CSNHCH_2CH_3$, $CSNHCH(CH_3)_2$, $CSNHC(CH_3)_3$, CSNH-3-pyridyl, CSNH-2,3,4-$C_6H_2F_3$, CSNH-4-$C_6H_4F$, CSNH-3,5-$C_6H_3F_2$, CSNH-2,6-$C_6H_3F_2$, CSNH-2-Cl-4-$NO_2C_6H_3$, CSNH-2-F-4-$BrC_6H_3$, CSNH-4-$C_6H_4NO_2$, CSNH-3-$CF_3$-4-Cl—$C_6H_3$, CSNH-2-F-5-$CF_3$-$C_6H_3$, CSNH-2-$CF_3$-4-F—$C_6H_3$, CSNH-3-$CF_3$-4-F—$C_6H_3$, CSNH-2-$C_6H_4OCF_3$, CSNH-4-$C_6H_4$OCF$_3$, CSNH-4-$C_6H_4$CF$_3$, CSNH-2-$C_6H_4$SCF$_3$, CSNH-3-$C_6H_4$CN, CSNH-4-$C_6H_4$CN, CSNH-2-$C_6H_4$OCHF$_2$, CSNH4-$C_6H_4$OCHF$_2$, CSNH-4-$C_6H_4$OCH$_3$, CSNH-3-$C_6H_4$CH$_3$, CSNH-2-OCH$_3$-4-NO$_2$C$_6$H$_4$, CSNH-4-$C_6H_4$SCH$_3$, CSNH-3,5-(CF$_3$)$_2$—C$_6$H$_4$, CSNH-3,4,5-(CH$_3$)$_3$C$_6$H$_2$, CSNH-1-naphthyl and CSNH-2-naphthyl; or a pharmaceutically acceptable salt thereof; or a pharmaceutical isomer thereof; or a combination of the same.

19. An antimycobacterial compound which comprises the formula:

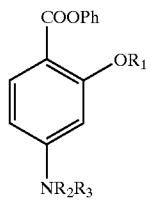

wherein $R_1$=H, $R_2$=H, and $R_3$=CSNHC$_6$H$_5$, CSNH-4-C$_6$H$_4$Br, CSNH-4-C$_6$H$_4$CH$_3$ and CSNH-4-C$_6$H$_4$Cl; or a pharmaceutically acceptable salt thereof; or a pharmaceutical isomer thereof; or a combination of the same.

20. An antimycobacterial compound which comprises the formula:

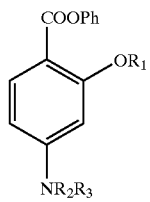

wherein $R_1$=H, $R_2$=H, and $R_3$=CSNHC$_6$H$_5$; or a pharmaceutically acceptable salt thereof; or a pharmaceutical isomer thereof; or a combination of the same.

21. The antimycobacterial compound according to claim 3 where $R_5$=trifluoromethyl, trichloromethyl, dichloromethyl, chloromethyl, trideuteriomethyl, iodomethyl, propenyloxy, difluorochloromethyl, pentafluoroethyl, or perfluoropropyl.

22. The antimycobacterial compound according to claim 3 where $R_6$=trifluoromethyl, trichloromethyl, dichloromethyl, chloromethyl, trideuteriomethyl, iodomethyl, propenyloxy, difluorochloromethyl, pentafluoroethyl, or perfluoropropyl.

23. A method for synthesizing a compound comprising the formula:

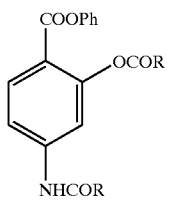

where R=trifluoromethyl, trichloromethyl, dichloromethyl, chloromethyl, trideuteriomethyl, iodomethyl, propenyloxy, difluorochloromethyl, pentafluoroethyl, or perfluoropropyl,
which comprises adding para-aminosalicylic acid phenyl ester with a carboxylic acid anhydride comprised of the formula:

(RCO)$_2$O where R=$C_1$ to $C_{14}$ alkyl, $C_1$ to $C_{14}$ substituted alkyl, $C_1$ to $C_{10}$ alkoxy, $C_1$ to $C_{10}$ substituted alkoxy, benzyloxy, substituted benzyloxy, steroidal, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle;

or with a mixed anhydride of the formula:

CF$_3$SO$_3$COCF$_3$ to form a reaction mixture, the reaction mixture characterized in that the mole ratio of para-aminosalicylic acid phenyl ester to carboxylic acid anhydride is about 0.06 to 1.00;
refluxing the reaction mixture;
cooling the reaction mixture; and
drying the reaction mixture to produce compound XIII.

24. A method for synthesizing a compound comprising the formula:

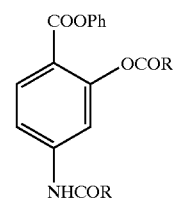

where R=$C_1$ to $C_{14}$ alkyl, $C_1$ to $C_{14}$ substituted alkyl, $C_1$ to $C_{10}$ alkoxy, $C_1$ to $C_{10}$ substituted alkoxy, benzyloxy, substituted benzyloxy, steroidal, $C_2$–$C_{20}$ substituted alkenyloxy, $C_2$ to $C_{10}$ alkenyl, $C_2$–$C_{10}$ substituted alkenyl, $C_2$ to $C_9$ substituted dialkenyl, $C_3$ to $C_7$ cycloalkyl, $C_3$ to $C_7$ substituted cycloalkyl, phenyl, substituted phenyl, aminoalkyl, substituted aminoalkyl, $C_7$ to $C_{16}$ phenylalkyl, $C_7$ to $C_{16}$ substituted phenylalkyl, benzyl, substituted benzyl, naphthyl, substituted naphthyl, heterocycle, or substituted heterocycle,
which comprises adding para-aminosalicylic acid phenyl ester with a carboxylic acid anhydride comprised of the formula:

(RCO)$_2$O where R=trifluoromethyl, trichloromethyl, dichloromethyl, chloromethyl, trideuteriomethyl, iodomethyl, propenyloxy, difluorochloromethyl, pentafluoroethyl, or perfluoropropyl, or with a mixed anhydride of the formula:

CF$_3$SO$_3$COCF$_3$ to form a reaction mixture, the reaction mixture characterized in that the mole ratio of para-aminosalicylic acid phenyl ester to carboxylic acid anhydride is about 0.06 to 1.00;
refluxing the reaction mixture;
cooling the reaction mixture; and
drying the reaction mixture to produce compound XIII.

* * * * *